United States Patent [19]

Kemper

[11] 4,261,879
[45] Apr. 14, 1981

[54] TINTED PIT AND FISSURE SEALANT

[75] Inventor: Russell N. Kemper, Flemington, N.J.

[73] Assignee: Johnson & Johnson Dental Products Company, East Windsor, N.J.

[21] Appl. No.: 83,896

[22] Filed: Oct. 11, 1979

[51] Int. Cl.³ .............................................. C08K 5/11
[52] U.S. Cl. .............................. 260/42.52; 260/998.11
[58] Field of Search .......................... 260/42.52, 998.11

[56] References Cited

U.S. PATENT DOCUMENTS

| | | | |
|---|---|---|---|
| 3,539,533 | 11/1970 | Lee et al. | 260/42.52 |
| 4,150,012 | 4/1979 | Joos | 260/42.52 |
| 4,188,317 | 2/1980 | Temin | 260/42.52 |

Primary Examiner—Lewis T. Jacobs
Attorney, Agent, or Firm—Charles J. Metz

[57] ABSTRACT

A composition is disclosed that is useful for sealing pits and fissures in teeth to prevent the formation of decay therein. The composition contains at least one colorant selected from the group consisting of a plant extract from Annatto or Turmeric, or $\beta$-Apo-8'-Carotenal.

7 Claims, No Drawings

TINTED PIT AND FISSURE SEALANT

The invention relates to a composition for sealing pits and fissures in tooth surfaces to prevent for reduce the formation of decay therein.

BACKGROUND OF THE INVENTION

Occlusal caries (decay) account for nearly half of all caries occurring in the human population. Certain adhesive materials have been shown to be effective in sealing the pits and fissures of the occlusal tooth surface, to thereby prevent or reduce the incidence of various attacks. One of the deficiencies of existing pit and fissure sealants is that colorless nature makes it difficult for the dentist to evaluate the integrity of the protective sealant during periodic examination, and also during application of the sealant to make sure that all the desired surfaces have been coated or, alternatively, to make sure that an excessive amount of coating has not been applied to certain areas. Inorganic pigments have been used to render the sealant more visible, such as the titanium dioxide pigment disclosed in U.S. Pat. No. 4,150,012. However, such inorganic pigments alter the viscosity of the sealant which can affect the sealant's properties. Further, the pigments tend to render the sealant opaque which makes it impossible for the dentist to visually assess the status of the tooth enamel under the sealant.

There has not been available a suitable sealant composition which can be readily detected on the tooth's surface, yet which is still transparent enough to permit the dentist to visually examine the surface of the tooth through the sealant. For esthetic reasons, only lighter color dyes are acceptable. Dark colors such as black, blue, and green are not esthetically pleasing and are, therefore, unacceptable.

Since sealants are used in the mouth, only dyes which are judged safe for internal use should be considered In the United States, the Food and Drug Administration (FDA) has listed compounds which can be certified for use in foods, drugs, and cosmetics (FD&C), and those which can be certified for use in drugs and cosmetics, D&C. Unfortunately, all but one of the FD&C certified dyes have been found to be insufficiently soluble in acrylic sealants to be usable therein, and the one having sufficient solubility (Red No. 3), is also water-soluble and tends to leach out in the presence of water. Also, all of the D&C colorants which are soluble in organic compounds are currently restricted to very specific uses, none of which include the use of coloring dental restorative materials. Thus, none of the certified dyes which one skilled in the art would select can be used for tinting a pit and fissure sealant if one adheres to FDA guidelines.

Another class of coloring agents which can be used in foods in the United States includes vegetable and plant extracts. These materials and their extraction method are described in the U.S. Code of Federal Regulations 21, part 73. These compounds being natural products, are usually water soluble and are therefore unacceptable for use in an organic monomer such as an acrylic sealant. A few of these plant extracts are soluble in animal fats and vegetable oils and are used to color such products as butter, cheese, margarine, and vegetable oils. Typical examples of such products are Annatto, Turmeric, and $\beta$-Apo-8'-Carotenal. However, from the structure of the principal colorant contained in each of the above, one would not expect these materials to be acceptable for use in a free radical polymerized acrylic system. All of these compounds derive their color from a highly conjugated vinyl system. Thus, one would expect these bonds to be attacked during the free radical polymerization of the chemically similar vinyl monomers, which would result in a disruption of the chromophore with subsequent loss of color. Further, one would also expect that the Curcumin, which is found in Turmeric extract, to act as an anti-oxidant to retard polymerization because it contains phenolic groups.

SUMMARY OF THE INVENTION

In accordance with this invention, it has been found that tinted pit and fissure sealant useful for applying to tooth surfaces for the prevention or reduction of dental caries can be produced from a composition comprising a polymerizable resin system containing acrylic monomer and at least one colorant selected from the group consisting of Annatto extract, Turmeric extract, and $\beta$-Apo-8'-Carotenal.

DETAILED DESCRIPTION OF THE INVENTION

In one form of the invention, the resin system is provided in a two-part package. In one package, there is contained polymerizable monomers and a polymerization catalyst such as peroxide. In the other package, there is contained polymerizable monomer and an accelerator to activate the catalyst. The colorant can be added to either or both of the packages, but is ordinarily added to the portion containing the polymerization catalyst accelerator.

The resin systems are formulated to have a viscosity that can be readily handled by the dentist, and will usually have a viscosity of less than 1200 centiposes, and preferably, from about 100 to about 600 centiposes at 25° C. Suitable resins include the Bowen monomer bisphenol-A diglycidyl dimethacrylate (bis-GMA), bisphenol-A dimethacrylate, triethylene glycol dimethacrylate, and other similar acrylic monomers which are well known in the art. Other acrylic formulations suitable for use in the invention are described in U.S. Pat. No. 3,815,239 and in the aforementioned U.S. Pat. No. 4,150,012.

The resin composition employs a polymerization catalyst, usually a peroxide catalyst such as benzoyl peroxide. The catalyst is used in the customary amounts. The system also employs an accelerator to activate the peroxide. Such accelerators are well known in the art, and are usually amines, with N,N-bis(2-hydroxyethyl)-3,4-dimethylaniline being the preferred accelerator.

Stabilizers such as substituted phenols may also be employed in the pit and fissure sealant composition of the invention to retard or prevent premature polymerization.

Alternatively, a one package acrylic resin system may be employed which uses a light activatable photoinitiation catalyst instead of a free radical catalyst plus accelerator. Ultraviolet light activatable photoinitiators that can be employed are described by Osborne et al. in U.S. Pat. No. 3,759,807, and visible light photopolymerization initiators are described by Dart et al., U.S. Pat. No. 4,071,424. Such photoinitiators are employed in the customary amounts in this invention.

The coloring agent employed in this invention is either Annatto extract powder, Turmeric extract powder, or β-Apo-8′-Carotenal. The active materials in these three colorants are shown in the following formulas:

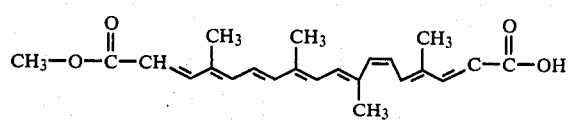

Cis-Bixin in Annatto Extract

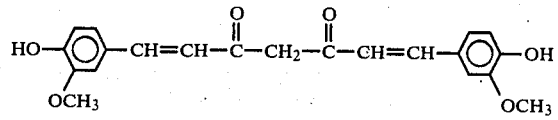

Curcumin in Turmeric Extract

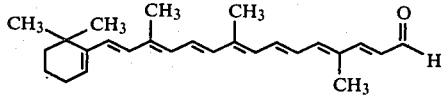

B-Apo-8′-Carotenal from citrus fruit and other sources

The colorant is employed in the invention in an effective amount, such as from about 0.01 to about 0.4 weight percent, based upon the weight of acrylic resin contained in the system. Solubility may be the limiting factor; otherwise, the proportion has not been found to be critical.

The following examples illustrate the practice of the invention:

EXAMPLE 1

A two-part liquid pit and fissure sealant was made from the following formulation:

| Component | Parts, by weight | |
|---|---|---|
| | Liquid A | Liquid B |
| Bis-GMA (Bisphenol-A diglycidyl dimethacrylate) | 40.50 | 40.50 |
| BADM (Bisphenol-A dimethacrylate) | 4.50 | 4.50 |
| TEGDM (Triethylene glycol dimethacrylate) | 55.00 | 55.00 |
| BHT (3,5-di-t-butyl-p-cresol) | 0.05 | 0.15 |
| Benzoyl peroxide | — | 2.00 |
| N,N-bis(2-hydroxyethyl)-3,4-dimethyl-aniline | 2.40 | — |
| Annatto extract powder | 0.07 | — |

The Annatto extract powder is preferably added to Liquid A under moderate heating (e.g., to about 50° C.). The heating facilitates dissolution and appears to give a more color stable product.

The two liquids are mixed in approximately equal proportions and are applied to the occlusal surface of the tooth after etching the tooth with, for example, 30-40 weight percent aqueous phosphoric acid, rinsing, and thoroughly drying.

The mixture of the two liquids has a dark brownish-purple color which changes abruptly to a light amber at the point at which the polymerizing liquid solidifies. This color change provides a built-in gel time indicator.

EXAMPLE 2

A two-part liquid pit and fissure sealant was made from the following formulation:

| Component | Parts, by weight | |
|---|---|---|
| | Liquid A | Liquid B |
| Bis-GMA (Bisphenol-A diglycidyl dimethacrylate) | 40.50 | 40.50 |
| BADM (Bisphenol-A dimethacrylate) | 4.50 | 4.50 |
| TEGDM (Triethylene glycol dimethacrylate) | 55.00 | 55.00 |
| BHT (3,5-di-t-butyl-p-cresol) | 0.05 | 0.15 |
| Benzoyl peroxide | — | 2.00 |
| N,N-bis(2-hydroxyethyl)-3,4-dimethyl-aniline | 2.40 | — |
| β-Apo-8′-carotenal (20% in vegetable oil) | 0.05 | — |

The mixture of the two liquids has a dark brown color. The color disappears almost completely upon gelation. This mixture is useful as a pit and fissure sealant which is readily visible during application, but which is almost colorless afterwards.

EXAMPLE 3

A two-part liquid pit and fissure sealant was made from the following formulation:

| Component | Parts, by weight | |
|---|---|---|
| | Liquid A | Liquid B |
| Bis-GMA (Bisphenol-A diglycidyl dimethacrylate) | 40.50 | 40.50 |
| BADM (Bisphenol-A dimethacrylate) | 4.50 | 4.50 |
| TEGDM (Triethylene glycol dimethacrylate) | 55.00 | 55.00 |
| BHT (3,5-di-t-butyl-p-cresol) | 0.05 | 0.15 |
| Benzoyl peroxide | — | 2.00 |
| N,N-bis(2-hydroxyethyl)-3,4-dimethyl-aniline | 2.40 | — |
| Turmeric extract powder | 0.20 | — |

The mixture of the two liquids has a dark yellow color, which remains essentially unchanged after gelation. The hindered phenolic groups in the Curcumin have the effect of retarding the polymerization. To bring the polymerization time back to about the usual one to two minutes that the dental practicioner is accustomed to, the BHT antioxidant can be omitted from Liquid A and reduced in concentration in Liquid B.

Control Examples

Attempts to employ vegetable extract colorants of similar molecular structure were not successful. Canthaxanthin was not sufficiently soluble to give noticeable coloration to a typical sealant monomer formulation. β-Carotene precipitated from a similar formulation upon refrigerated storage. These materials have the following molecular structures:

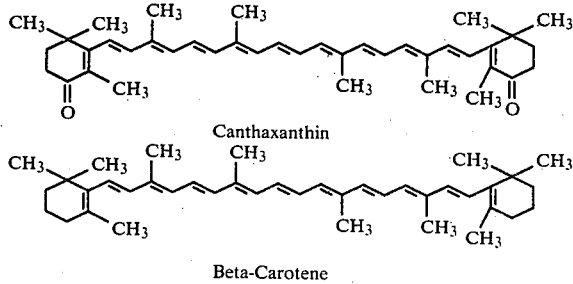

Canthaxanthin

Beta-Carotene

What is claimed is:

1. A dental pit and fissure sealant composition comprising a polymerizable resin system containing acrylic monomer, and a small amount, sufficient to impart visible color to said sealent composition, of a colorant selected from the group consisting of Annatto extract, Turmeric extract, and β-Apo-8'-carotenal.

2. The composition of claim 1 wherein the colorant is Annatto extract.

3. The composition of claims 1 or 2 wherein the colorant is employed in an amount of from about 0.01 to about 0.4 weight percent, based on weight of acrylic monomer.

4. The composition of claims 1 or 2 wherein the polymerizable resin system includes bisphenol-A diglycidyl dimethacrylate.

5. The composition of claim 4 wherein the polymerizable resin system includes a polyalkylene glycol dimethacrylate viscosity reducer.

6. The composition of claim 5 wherein the polyalkylene glycol dimethacrylate is triethylene glycol dimethacrylate, 7. The composition of claim 6 wherein the polymerizable resin system contains bisphenol-A dimethacrylate.

* * * * *